United States Patent [19]

Atwater

[11] Patent Number: 5,541,149
[45] Date of Patent: Jul. 30, 1996

[54] COMPOSITIONS COMPRISING A PHOSPHONIC COMPOUND, AND A SULFURIC ACID-AMIDE ADDUCT AND METHODS FOR CONTROLLING VEGETATION USING SUCH COMPOSITIONS

[75] Inventor: Mark L. Atwater, Iron City, Ga.

[73] Assignee: Union Oil Company of California, Los Angeles, Calif.

[21] Appl. No.: 335,191

[22] Filed: Nov. 7, 1994

Related U.S. Application Data

[63] Continuation of Ser. No. 989,044, Dec. 10, 1992, abandoned.

[51] Int. Cl.⁶ .................................. A01N 57/04
[52] U.S. Cl. .................. 504/127; 504/165; 504/148; 504/173
[58] Field of Search .................. 504/127, 128, 504/148, 165, 173

[56] References Cited

U.S. PATENT DOCUMENTS

| | | | |
|---|---|---|---|
| 3,879,188 | 4/1975 | Fritz et al. | 71/86 |
| 4,445,925 | 5/1984 | Young | 71/28 |
| 4,447,253 | 5/1984 | Young | 71/28 |
| 4,728,466 | 3/1988 | Young et al. | 260/502.4 R |
| 4,840,660 | 6/1989 | Kowite et al. | 71/86 |
| 4,932,995 | 6/1990 | Escobar | 71/86 |
| 4,966,620 | 10/1990 | Young | 71/83 |
| 4,994,101 | 2/1991 | Young | 71/83 |
| 5,123,951 | 6/1992 | See et al. | 71/86 |

FOREIGN PATENT DOCUMENTS

| | | |
|---|---|---|
| 0243522 | 11/1987 | European Pat. Off. . |
| 0271173 | 6/1988 | European Pat. Off. . |
| 1505331 | 3/1978 | United Kingdom . |
| 2029832 | 3/1980 | United Kingdom . |
| 8302877 | 9/1983 | WIPO . |

OTHER PUBLICATIONS

Farm Chemicals Handbook 1990, Meister Publ. Co., Willoughby, OH (1990), pp. C18–C19, C118, C121.
Crop Protection Chemicals Reference, 7th Edition, Chemical and Pharmaceutical Press, New York, NY (1991), pp. 1838–1840.
Thomson, *Agricultural Chemicals Book III Miscellaneous Chemicals,* Thomson Publications, Freson, CA, pp. 60–65, (1988–89 Revision).
Database WPI, Week 7650, Derwent Publications Ltd., London, GB;AN 76-92566x [50]. (Oct. 13, 1976).
Database CHEMABS, Chemical Abstracts, Columbus, Ohio, U.S.A., vol. 9, No. 3, pp. 170–173 (1985).
Farm Chemical Handbook '91, Meister Publishing Co., Willoughby, OH, pp. C 124–125 and C127.

*Primary Examiner*—Allen J. Robinson
*Assistant Examiner*—Brian G. Bembenick
*Attorney, Agent, or Firm*—Gregory F. Wirzbicki; Shlomo R. Frieman

[57] ABSTRACT

A composition exhibiting increased defoliation and growth inhibition efficacy comprises the mixture of an amide-sulfuric acid adduct and a phosphonic acid and/or phosphonic acid derivative or salt.

26 Claims, 1 Drawing Sheet

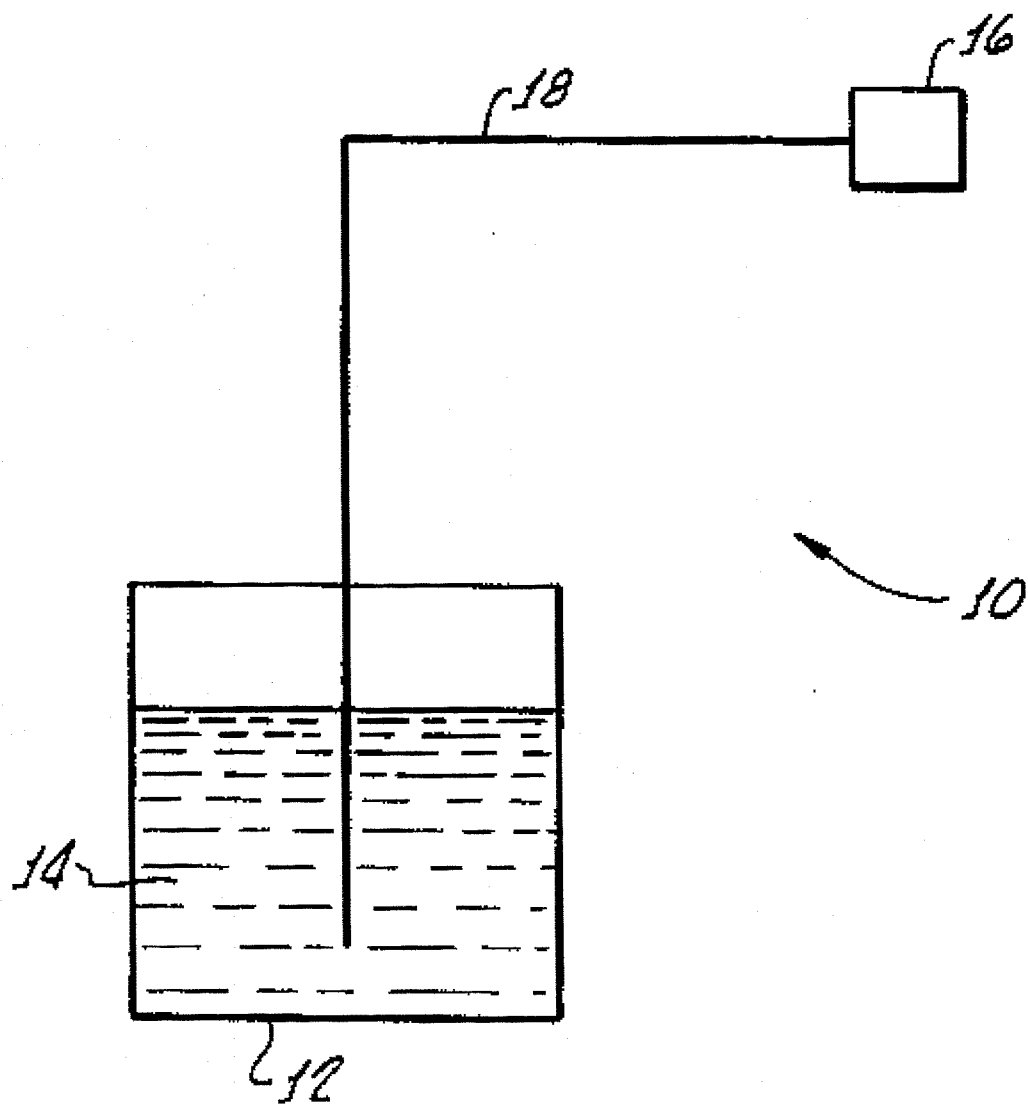

COMPOSITIONS COMPRISING A PHOSPHONIC COMPOUND, AND A SULFURIC ACID-AMIDE ADDUCT AND METHODS FOR CONTROLLING VEGETATION USING SUCH COMPOSITIONS

This application is a continuation, of application Ser. No. 07/989,044, filed Dec. 10, 1992 (Abandoned).

BACKGROUND

The present invention relates to compositions and methods for regulating plant growth, to devices for spraying such compositions, and to land and plants coated with plant growth regulators.

(2-Chloroethyl)phosphonic acid or ethephon is a known plant growth regulator.

SUMMARY OF THE INVENTION

There is a need for increasing the defoliation and/or growth inhibition efficacy of ethephon. The present invention satisfies this need by providing a composition formed by mixing ethephon and an amide-sulfuric acid adduct. This composition has significantly increased defoliation and growth inhibition efficacy. In addition to or in place of ethephon, the composition optionally comprises one or more other phoshonic acids, phosphonic acid derivatives, or salts thereof.

The present invention also provides a method for controlling vegetation, an apparatus for applying the composition, and a plot of land and a plant having at least a portion of their surfaces in contact with the composition. The method comprises the step of applying to vegetation an effective amount of the composition.

Regarding the apparatus, such apparatus comprises (a) a tank or other device for holding the composition and (b) a sprayer or other means for dispersing the composition, the sprayer being in communication (e.g., fluid communication) with the tank. The apparatus is characterized in that the composition of the present invention is present within the tank.

BRIEF DESCRIPTION OF DRAWING

The potentiation in the defoliation and/or growth inhibition efficacy of ethephon and other features, aspects, and advantages of the present invention will become better understood with reference to the following description, appended claims, and accompanying drawing where the sole FIGURE is a schematic representation of a spraying apparatus 10 comprising a container 12 for containing the composition 14 of the present invention, a sprayer 16 for spraying the composition 14, and a conduit or other device 18 for transporting the composition 14 from the container 12 to the sprayer 16 or otherwise maintaining the container 12 and the sprayer 16 in fluid communication.

DETAILED DESCRIPTION OF THE INVENTION

The phosphonic acids and phosphonic acid derivatives employed in the present invention have the formula I

where $X_1$ is chalcogen; $R_1$ is selected from the group consisting of halo-ethyl and phosphono-ethyl; $R_2$ and $R_3$ are independently selected from the group consisting of (a) halogen and (b) $-X_2-R_4$, $-X_2-CH_2-R_4$, $X_2$ being a chalcogen and $R_4$ being selected from the group consisting of hydrogen, unsubstituted aryl, substituted aryl, heterocyclic groups, unsubstituted alkyl, substituted alkyl, unsubstituted cycloalkyl, substituted alkyl, alkene, and alkyne, provided that when one $R_4$ is selected from the group consisting of unsubstituted alkyl, substituted alkyl, unsubstituted cycloalkyl, substituted alkyl, alkene, and alkyne, the other $R_4$ is selected from the group consisting of unsubstituted aryl, substituted aryl, and heterocyclic groups. When $R_2$ and $R_3$ are taken together, they form the group $-R_5-R_7-R_6-$, $R_5$ and $R_6$ each being connected to the phosphorous atom by a separate single bond and one of $R_5$ and $R_6$ being a chalcogen and the other being selected from the group consisting of chalcogen, $-X_3-CH_2-$, $-CO-O-$, and $-CONH_2$, $X_3$ being a chalcogen, and $R_7$ being a cyclic group selected from the group consisting of benzene, substituted benzene, heterocyclic ring, and substituted heterocyclic ring. In addition, when one of $R_2$ and $R_3$ is $-X_4-R_8$, the other is

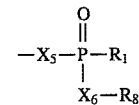

$R_8$ being independently selected from the group consisting of hydrogen, unsubstituted alkyl, substituted alkyl, unsubstituted cycloalkyl, substituted cycloalkyl, unsubstituted aryl, substituted aryl, and heterocyclic groups, and $X_4$, $X_5$, and $X_6$ being chalcogen.

When the carbon atom content of a carbon-containing radical is not specified in the specification or claims, the radical generally contains up to about 20 carbon atoms. In addition, each alkyl and cycloalkyl group preferably contains up to about 18 carbon atoms, more preferably up to about 12 carbon atoms, and most preferably up to about 6 carbon atoms.

As used in the specification and claims the term "chalcogen" means the group VI elements (e.g., oxygen, sulfur, selenium, and tellurium, with the preferred chalcogens being oxygen and sulfur, and the most preferred being oxygen); and the term "halo" or "halogen" means the group VII elements (e.g., fluorine, chlorine, bromine, and iodine, with the preferred halogens being chlorine and bromine, and the most preferred being chlorine).

Specific phosphonic acids and phosphonic acid derivatives employed in the present invention include, but are not limited to:

1. The bis(acid chloride) of (2-chloroethyl)phosphonic acid.
2. The pyrocatechol cyclic ester of (2-chloroethyl)phosphonic acid.
3. The 4-chloropyrocatechol cyclic ester of (2-chloroethyl)phosphonic acid.
4. The mixed ethyl and 2-hydroxyphenyl diester of (2-chloroethyl)phosphonic acid.

5. The mixed butyl and 2-hydroxyphenyl diester of (2-chloroethyl)phosphonic acid.
6. The mixed propynyl and 2-hydroxyphenyl diester of (2-chloroethyl)phosphonic acid.
7. The 2-chloroethyl monoester of (2-chloroethyl)phosphonic acid.
8. (2-bromoethyl)phosphonic acid.
9. The bis(phenyl) ester of (2-chloroethyl)phosphonic acid.
10. The tetrachloropyrocatechol cyclic ester of (2-chloroethyl)phosphonic acid.
11. (2-iodoethyl)phosphonic acid.
12. The saligen cyclic ester of (2-chloroethyl)phosphonic acid.
13. The salicyclic acid cyclic ester of (2-chloroethyl)phosphonic acid.
14. (Phosphonoethyl)phosphonic acid.
15. (Phosphonoethylthioethyl)phosphonic acid.
16. The 3-hydroxyphenyl monoester of (2-chloroethyl)phosphonic acid (which exists in polymeric form).
17. The bis(2-oxo-pyrrolidinylmethyl) ester of (2-chloroethyl)phosphonic acid.
18. The o-hydroxyphenyl monoester of (2-chloroethyl)phosphonic acid.
19. The mixed isopropyl and 2-hydroxyphenyl diester of (2-chloroethyl)phosphonic acid.
20. (2-fluoroethyl)phosphonic acid.
21. The mixed octyl and 2-hydroxyphenyl diester of (2-chloroethyl)phosphonic acid.
22. The mixed hexadecyl and 2-hydroxyphenyl diester of (2-chloroethyl)phosphonic acid.
23. The mixed tridecyl and 2-hydroxyphenyl diester of (2-chloroethyl)phosphonic acid.
24. The anhydride of (2-chloroethyl)phosphonic acid.
25. (2-chloroethyl)phosphonic acid.
26. The 2-chloroethyl-butylester, 2-hydroxyphenylester of phosphonic acid.
27. The 2-chloroethyl-2-chloroethylester of phosphonic acid.
28. The salicyclic acid cyclic ester of phosphonoamidic acid.
29. The mixed phenyl and 2-hydroxyphenyl diester of (2-chloroethyl)phosphonic acid.
30. 2-chloroethyl-dichlorophosphine.
31. The bis(pentachlorophenyl) ester of (2-chloroethyl)phosphonic acid.
32. (2-chloropropyl)phosphonic acid.
33. (2-phenylthioethyl)phosphonic acid.
34. The 2,3-pyridinedio cyclic ester of (2-chloroethyl)phosphonic acid.
35. (2-chloroethyl)thiophosphonic acid.
36. 2-chloroethyl-2,3-dibromo-4-hydroxy-2-butyenyl ester polymer.

Salts of the foregoing phosphonic acids are optionally employed in the present invention. Exemplary salts include, but are not limited to, the salts of alkali metals, alkaline earth metals, aluminum, ammonium, and zinc. The preferred alkali metals are lithium, sodium, and potassium, and the preferred alkaline earth metals are calcium and magnesium.

The preferred phosphonic acid and phosphonic acid derivatives have the formula II

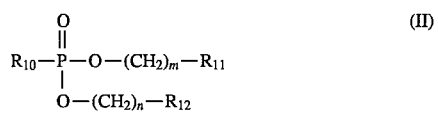

wherein one of m or n is 0 and the other is 0 or 1; $R_{10}$ is haloethyl or phosphono-ethyl; $R_{11}$ is a hydrogen atom or a substituted or unsubstituted phenyl group; and $R_{12}$ is a hydrogen atom or a substituted or unsubstituted phenyl group or a halogen-substituted or unsubstituted, saturated or unsaturated hydrocarbon chain containing from 2 to about 12 carbon atoms. Preferably, $R_{10}$ is haloethyl, with (2-chloroethyl)phosphonic acid embodying the preferred acid and $C_1$ to $C_3$ alkyl esters and diesters of (2-chloroethyl)phosphonic acid being the preferred ester derivatives.

The phosphonic acids, phosphonic acid derivatives, and their salts (hereinafter collectively referred to as "phosphonic compounds") employed in the present invention are synthesized using techniques well known to those skilled in the art. See, for example, U.S. Pat. No. 5,123,951, U.S. Pat. No. 4,932,995, U.S. Pat. No. 4,840,660, U.S. Pat. No. 4,728,466, and U.S. Pat. No. 3,879,188, which patents are incorporated herein in their entireties by reference.

The adducts employed in the present invention are produced by reacting, under controlled conditions, sulfuric acid with an amide having the formula III

wherein X is a chalcogen, each of $R_{20}$ and $R_{21}$ is independently selected from hydrogen and monovalent radicals, and $R_{20}$ and $R_{21}$, when taken together, form a divalent radical.

As used in the specification and claims, the term "amide" includes all components of formula III regardless of the chalcogen employed. Preferably, the radical is selected from the group consisting of (i) cyclic, acyclic, straight, branched, aryl, aralkyl, and alkaryl groups which optionally contain one or more (a) heteroatoms such as sulfur, nitrogen, oxygen, and phosphorus and/or (b) substituents such as thiol, hydroxy, nitro, amino, nitrile, amide, ester, and halogen groups and (ii) substituted and unsubstituted amines. The preferred radicals are free of olefinic and alkynyl unsaturation and generally contain up to about 20, preferably up to about 10 carbon atoms per radical.

Exemplary amides include, but are not limited to, urea, thiourea, formamide, biuret, triuret, thioformamide, acetamide, N-methylbenzamide, 3-chloro-N-ethylbutyramide, N-phenylacetamide, N-phenylproprionamide, dimethylformamide, ethyl formamide, methyl formamide, propionamide, butyramide, valeramide, benzamide, and succinamide. The preferred amides are urea, thiourea, formamide, biuret, triuret, thioformamide, dimethylformamide, ethyl formamide, and methyl formamide, with urea being the most preferred amide.

To ensure that at least some of the sulfuric acid is present as the monoamide-sulfuric acid adduct, it is preferred that the molar ratio of amide to sulfuric acid be about ¼ to about ⁷⁄₄, more preferably about ½ to about ³⁄₂, and most preferably about ¹⁄₁ to about ³⁄₂.

Methods for making the adduct or sulfuric acid-amide reaction product are well known to those skilled in the art. See, for example, U.S. Pat. No. 4,994,101, U.S. Pat. No. 4,966,620, U.S. Pat. No. 4,447,253, and U.S. Pat. No. 4,445,925, which patents are incorporated herein in their entireties by reference.

The combination of the present invention is used advantageously to control vegetation. The efficacy for growth control depends, among other things, on the amount of the combination applied per hectare (acre), the relative proportions of the adduct to the phosphonic compound, the treatment time, and the type of plant to which it is applied. The defoliation and growth inhibition effects exhibited by the combination are significantly better than those observed when the phosphonic compound is employed alone.

The combination of the present invention is used as a plant growth regulator on vegetation, including but not limited to, apples, barley, blackberries, bromeliads, cantaloupes, cherries, coffee, cotton, cranberries, cucumbers, figs, filberts, grapes, guava, lemons, Macadamia nuts, ornamentals, peppers, pineapples, rye, squash, tangerines, tangerine hybrids, tobacco, tomatoes, walnuts, wheat, rape, corn, flax, maize, oranges, peaches, rubber, and sugarcane.

While the combination of the present invention can be used alone, it generally is applied to plants in conjunction with other substances, such as, carrier vehicles, wetting agents, emulsifiers, and solvents. Exemplary carrier vehicles include water, aliphatic or aromatic hydrocarbons, such as benzene, toluene, xylene, cyclohexonone, isophorone, and mineral or vegetable oil fractions. The particularly preferred carrier vehicle is water, based on its availability and cost. Alternatively, of course, a solid carrier vehicle could be utilized. Examples of solid carrier vehicles are minerals, such as siliceous clay, silica gel, talc, kaolin, limestone, and plant products (e.g., flours).

Typical surface active substances which may be utilized include calcium-lignin sulfonate, polyoxyethyleneoctylphenol ether and naphthalene-sulfonic acids and their salts, phenolsulfonic acids and their salts, formaldehyde condensates, fatty alcohol sulfates, and substituted benzenesulfonic acids and their salts.

The combined concentrations of the phosphonic compound and the adduct in the composition of the present invention is generally at least about 60, preferably at least about 70, and more preferably at least about 85, weight percent based upon the total weight of the composition. For field application to plants, the composition is typically diluted to contain from about 1 to about 80 weight percent of the active agents, about 20 to about 99 weight percent of a solid or liquid carrier vehicle, and optionally up to about 20 weight percent of a surface-active substance. (As used in the specification and claims, the term "active agents" means the phosphonic compounds and the adducts employed in the present invention.)

The ratio of the moles of the adduct to the moles of the phosphonic compound is typically about 0.1:1 to about 100:1. Preferably, the mole ratio is about 0.5:1 to about 50:1, more preferably about 1:1 to about 25:1, and most preferably about 1.5:1 to about 10:1. When the adduct and phosphonic acid have similar molecular weights, such as in the case of ethephon (molecular weight about 145) and monocarbamide dihydrogen sulfate (molecular weight about 186), the general and preferred ranges for the ratio of the weight of the adduct to the weight of the phosphonic compound are comparable to the above mole ratio ranges.

The combination of the present invention has been found to be highly effective for defoliation and growth inhibition control of plants, such as cotton, when the amount of the phosphonic compound applied is at least about 0.56 (about 0.5), preferably about 0.56 to about 11.2 (about 0.5 to about 10), and more preferably about 0.84 to about 5.6 (about 0.75 to about 5), kilograms per hectare (kg/H) (pounds per acre (lb/A)). In terms of moles, generally at least about 2.5 (about 1), preferably about 2.5 to about 37.5 (about 1 to about 15), more preferably about 3.75 to about 25 (about 1.5 to about 10), and most preferably about 5 to about 20 (about 2 to about 8), moles per hectare (m/H) (moles per acre (m/A)) of the phosphonic compound are applied.

When the composition of the present invention is sprayed from the ground, it is generally diluted with a carrier vehicle (e.g., water) to provide a spray volume from about 9.4 (about 1) to about 1,870 (about 200) liters per hectare (l/H) (gallons per acre (GPA)). Preferably, a spray volume of about 93.5 to about 467.5 l/H (about 10 to about 50 GPA) is utilized. In the case of aerial spraying, a more concentrated solution is commonly used and typically applied at a rate of about 18.7 to about 140.3 (about 2 to about 15), and preferably about 28.1 to about 46.8 (about 3 to about 5), l/H (GPA).

While the composition is generally intended to primarily contact the sprayed vegetation, a portion of the composition also contacts the land supporting the particular crop being sprayed. Typically, at least about 0.001 percent, more commonly at least about 0.01 percent, and most commonly at least about 0.1 percent, of the land surface area of the sprayed field is contacted by the composition of the present invention. For example, if a crop standing on about 0.4 hectare (about 1 acre) of land is sprayed with the composition of the present invention, the amount of the land whose surface is contacted by the composition is generally at least about 0.0004 hectare (about 0.001 acre), more commonly at least about 0.004 hectare (about 0.01 acre), and most commonly at least about 0.04 hectare (about 0.1 acre). Preferably, less than about 50 percent, more preferably less than about 25 percent, even more preferably less than about 10 percent, and most preferably less than about 5 percent of the land surface of the field is contacted by the sprayed composition.

EXAMPLE

The following example is intended to illustrate, and not limit, the invention. The example details a number of field tests which demonstrate the increased defoliation and growth inhibition efficacy of exemplary combinations within the scope of invention when compared to controls containing just a phosphonic compound as the active ingredient.

Methodology

The test site was located on a Tifton sandy loam soil (about 0–2% slope). A 3×4 factorial experiment in a randomized complete block, split-plot configuration was utilized. Three rates of ethephon (available from Rhone-Poulenc as an aqueous solution containing about 0.7 kilograms per liter (kg/l) (about 1.5 pounds per quart (lb/qt)) of active ingredient (namely, (2-chloroethyl)phosphonic acid)) served as main plots, while four rates of Enquik® brand monocarbamide dihydrogen sulfate (MCDS) were the subplots. (Enquik is commercially available from the Union Oil Company of California. Enquik is an aqueous liquid containing approximately 82 weight percent (about 1.2 kg/l (about 2.6 lb/qt) MCDS.) DPL 90 cotton was planted. The plots consisted of two rows (about 1.8 m×about 9.1 m (about 6 ft×30 ft) per row), with two nontreated buffer rows between the plots. Replicates were separated by about 3 m (about 10 ft) alleys. Application was made using a $CO_2$ backpack sprayer (4 nozzles on about 45.7 cm (about 18 in) centers) calibrated to deliver about 233.8 l/H (about 25 GPA) using TJ11002 flat fan nozzles at about 446.1 kpascal (about 50 psi) and about 4.8 km per hour (about 3 miles per hour (mph)) ground speed. Application was made about 43 days after planting to cotton about 25.4 to about 40.6 cm (about 10 to about 16 in) tall with about 7–12 leaves per plant. Additional spray adjuvants were not used. Details of application and environmental conditions are listed in the following Table A.

TABLE A

| Environmental Conditions | |
|---|---|
| Starting Time | 3:20 pm |
| Finish Time | 4:30 pm |
| Air Temperature | 36.1° C. (97° F.) |
| Soil Temperature | 36.7° C. (98° F.) |
| Relative Humidity | 50% |
| Cloud Cover | 30% |
| Wind (Speed/Direction) | 0–6.4 km per hr/W (0–4 mph/W) |
| Soil Moisture | Dry |
| Leaf Surface Moisture | Dry |
| Crop Height | 25.4–40.6 cm (10–16 in) |
| Crop Stage | 7–12 leaf/prebloom |
| Application Parameters | |
| Application Timing | P.O.T.[1] |
| Application Method | $CO_2$ Backpack |
| Equipment Speed | 3.8 km/h (3 mph) |
| Nozzle Size | Flat Fan 11002 |
| Nozzle Spacing | 45.7 cm (18") |
| Nozzle Height | 76.1 cm (30") |
| Swath Width | 1.8 m (6') |
| Spray Pressure | 446.1 kpascal (50 psi) |
| Spray Volume | 233.8 l/H (25 GPA) |

[1]·P.O.T. denote post emergent over the top.

Due to a plot map interpretation error, application was made with MCDS rate as the main plots and ethephon rate as the sub-plots. As a result, all analyses were conducted using a standard two-way Analysis of Variance (A.N.O.V.A.).

Visual ratings of percent defoliation (0–100) were made about 3 and 7 days after application or treatment (D.A.T.). Visual evaluation of percent height reduction (0–100) was made about 7 D.A.T. Assessment of terminal regrowth was made by counting the number of apical meristems exhibiting regrowth (i.e., newly emerged leaf or leaves) from about 50 plants per plot at about 8 D.A.T. These counts were made only on treatments containing about 2.34 l/H (about 1 quart per acre (qt/A)) ethephon. Visual assessment of percent growth inhibition (0–100) was made about 14 D.A.T. and again only on treatments containing about 2.34 l/H (about 1 qt/A) ethephon. All the data were analyzed using a two-way A.N.O.V.A. with appropriate mean separations conducted at about the 5% level of significance using Duncan's Multiple Range Test (DMRT; P=0.05). The results are shown below in Tables B–E.

TABLE B

Effect Of MCDS On Defoliation With Ethephon, 3 D.A.T.

| Treatment | Percent Defoliation (Visual) | | | | |
|---|---|---|---|---|---|
| | I | II | III | IV | AVERAGE |
| Ethephon (0.58 l/H (0.25 qt/A)) | 0 | 0 | 0 | 0 | 0 |
| +MCDS (2.34 l/H (1 qt/A)) | 15 | 5 | 5 | 0 | 6 |
| +MCDS (4.68 l/H (2 qt/A)) | 0 | 10 | 10 | 15 | 9 |
| +MCDS (7.02 l/H (3 qt/A)) | 10 | 10 | 10 | 5 | 9 |
| Ethephon (1.16 l/H (0.5 qt/A)) | 0 | 10 | 0 | 10 | 5 |
| +MCDS (2.34 l/H (1 qt/A)) | 40 | 35 | 35 | 25 | 34 |
| +MCDS (4.68 l/H (2 qt/A)) | 20 | 25 | 10 | 15 | 18 |
| +MCDS (7.02 l/H (3 qt/A)) | 20 | 30 | 25 | 15 | 23 |
| Ethephon (2.34 l/H (1 qt/A)) | 15 | 5 | 20 | 10 | 13 |
| +MCDS (2.34 l/H (1 qt/A)) | 25 | 20 | 20 | 10 | 20 |
| +MCDS (4.68 l/H (2 qt/A)) | 20 | 35 | 10 | 30 | 24 |
| +MCDS (7.02 l/H (3 qt/A)) | 40 | 45 | 40 | 35 | 40 |

TABLE C

Effect Of MCDS On Defoliation and Height Reduction With Ethephon, 7 D.A.T.

| Treatment | Percent Defoliation (Visual) | | | | | Percent Height Reduction (Visual) | | | | |
|---|---|---|---|---|---|---|---|---|---|---|
| | I | II | III | IV | AVERAGE | I | II | III | IV | AVERAGE |
| Ethephon (0.58 l/H (0.25 qt/A)) | 0 | 0 | 0 | 0 | 0 | 0 | 0 | 0 | 0 | 0 |
| +MCDS (2.34 l/H (1 qt/A)) | 5 | 10 | 10 | 0 | 6 | 10 | 10 | 10 | 10 | 10[1] |
| +MCDS (4.68 l/H (2 qt/A)) | 0 | 10 | 15 | 10 | 9 | 10 | 15 | 15 | 10 | 13[1] |
| +MCDS (7.02 l/H (3 qt/A)) | 20 | 25 | 10 | 10 | 16[1] | 20 | 25 | 15 | 15 | 19[1] |
| Ethephon (1.16 l/H (0.5 qt/A)) | 0 | 5 | 0 | 0 | 1 | 25 | 0 | 15 | 5 | 11 |
| +MCDS (2.34 l/H (1 qt/A)) | 30 | 30 | 25 | 45 | 33[1] | 50 | 35 | 30 | 35 | 38[1] |
| +MCDS (2.68 l/H (2 qt/A)) | 40 | 45 | 30 | 35 | 38[1] | 30 | 50 | 20 | 20 | 30[1] |
| +MCDS (7.02 l/H (3 qt/A)) | 60 | 35 | 45 | 40 | 45[1] | 45 | 30 | 50 | 50 | 44[1] |
| Ethephon (2.34 l/H (1 qt/A)) | 30 | 10 | 15 | 20 | 19 | 10 | 25 | 10 | 25 | 18 |
| +MCDS (2.34 l/H (1 qt/A)) | 50 | 60 | 50 | 45 | 51[1] | 50 | 50 | 40 | 40 | 45[1] |
| +MCDS | 50 | 50 | 50 | 60 | 53[1] | 40 | 40 | 40 | 50 | 43[1] |

TABLE C-continued

Effect Of MCDS On Defoliation and Height Reduction With Ethephon, 7 D.A.T.

| Treatment | Percent Defoliation (Visual) | | | | | Percent Height Reduction (Visual) | | | | |
|---|---|---|---|---|---|---|---|---|---|---|
| | I | II | III | IV | AVERAGE | I | II | III | IV | AVERAGE |
| (4.68 l/H (2 qt/A)) +MCDS (7.02 l/H (3 qt/A)) | 60 | 60 | 55 | 55 | 58[1] | 40 | 40 | 40 | 40 | 40[1] |

1. Significantly different using DMRT at P = 0.05.

TABLE D

Effect Of MCDS On Terminal Regrowth With Ethephon, 8 D.A.T.

| | Number Of Terminals With Regrowth[1] | | | | |
|---|---|---|---|---|---|
| Treatment | I | II | III | IV | Average |
| Ethephon (2.34 l/H (1 qt/A)) | 35 | 46 | 42 | 34 | 39 |
| +MCDS (2.34 l/H (1 qt/A)) | 8 | 22 | 15 | 4 | 12[2] |
| +MCDS (4.68 l/H (2 qt/A)) | 11 | 15 | 8 | 6 | 10[2] |
| +MCDS (7.02 l/H (3 qt/A)) | 10 | 5 | 7 | 5 | 7[2] |

1. Number of terminals per 50 plants in each plot exhibiting apical regrowth (newly emerged leaf or leaves).
2. Significantly different using DMRT at P = 0.05.

TABLE E

Effect Of MCDS On Growth Inhibition With Ethephon, 14 D.A.T.

| | Percent Growth Inhibition[1] | | | | |
|---|---|---|---|---|---|
| Treatment | I | II | III | IV | Average |
| Ethephon (2.34 l/H (1 qt/A)) | 30 | 35 | 20 | 25 | 28 |
| +MCDS (2.34 l/H (1 qt/A)) | 65 | 75 | 60 | 55 | 64[2] |
| +MCDS (4.68 l/H (2 qt/A)) | 60 | 60 | 50 | 60 | 58[2] |
| +MCDS (7.02 l/H (3 qt/A)) | 55 | 70 | 65 | 60 | 63[2] |

1. Visual estimation compared to nontreated buffer rows.
2. Significantly different using DMRT at P = 0.05.

Discussion

A. Defoliation

In view of above Tables B–C, the effect of the addition of MCDS to ethephon on cotton defoliation was similar at 3 and 7 D.A.T. Although the addition of MCDS to about 0.58 l/H (about 0.25 qt/A) ethephon improved defoliation, only the rate of about 7.02 l/H (about 3 qt/A) MCDS resulted in significant improvement. The addition of about 2.34 (about 1), about 4.68 (about 2), or about 7.02 (about 3) l/H (qt/A) MCDS to either about 1.16 (about 0.5) or about 2.34 (about 1) l/H (qt/A) ethephon resulted in a significant increase in cotton defoliation at 7 D.A.T. The addition of about 2.34 (about 1), about 4.68 (about 2), and about 7.02 (about 3) l/H (qt/A) MCDS to about 1.16 l/H (about 0.5 qt/A) ethephon resulted in about 33, 38, and 45% defoliation, respectively, compared to about 1% for ethephon alone. Similarly, the addition of about 2.34 (about 1), about 4.68 (about 2), and about 7.02 (about 3) l/H (qt/A) MCDS to about 2.34 l/H (about 1 qt/A) ethephon resulted in about 51, 53, and 58% defoliation, respectively, at 7 D.A.T., compared to about 19% for ethephon alone. There was no significant difference in defoliation among rates of MCDS when combined with about 2.34 l/H (about 1 qt/A) ethephon.

B. Growth Inhibition

As shown in Tables C–E, the effects on growth inhibition were measured at about 7, 8, and 14 D.A.T. Visual estimations of percent height reduction were taken at about 7 D.A.T. on all treatments, while apical regrowth counts (about 50 plants/plot at about 8 D.A.T.) and visual estimations of percent growth reduction (total canopy) were made at about 14 D.A.T. only on treatments containing about 2.34 l/H (about 1 qt/A) ethephon.

The results from all the growth measurements and ratings were similar in trend to those of defoliation. While the addition of about 2.34 l/H (about 1 qt/A) MCDS to about 0.58 l/H (about 0.25 qt/A) ethephon caused a numerical increase in height reduction, the addition of about 4.68 (about 2) or about 7.02 (about 3) l/H (qt/A) MCDS gave a statistically significant increase. The addition of about 2.34 (about 1), about 4.68 (about 2), or about 7.02 (about 3) l/H (qt/A) MCDS to either about 1.16 l/H (about 0.5 qt/A) or about 2.34 l/H (about 1 qt/A) ethephon significantly increased height reduction at 7 D.A.T. Similarly, the addition of all rates of MCDS to about 2.34 l/H (about 1 qt/A) ethephon caused a significant decrease in apical regrowth at 8 D.A.T. and a significant increase in growth reduction at 14 D.A.T. There was no significant difference in either height reduction, apical regrowth, or growth inhibition among the rates of MCDS in combination with about 2.34 l/H (about 1 qt/A) ethephon.

Although the present invention has been described in detail with reference to some preferred versions, other versions are possible. For example, the composition of the present invention can also be employed to (a) accelerate boll opening on cotton, (b) stunt plant height (e.g., height reduction of grain producing plants such as wheat), and (c) maintain plants in the vegetative state (e.g., delay or prevent flowering of ornamental plants). In addition, the mixing of the amide-sulfur adduct and the phosphonic compound, besides forming a mixture, also produces a reaction product. Therefore, the spirit and scope of the appended claims should not necessarily be limited to the description of the preferred versions contained herein.

What is claimed is:

1. A composition formed by mixing (a) a reaction product of sulfuric acid and an amide and (b) a compound selected from the group consisting of (2-chloroethyl)phosphonic acid and salts of (2-chloroethyl)phosphonic acid, wherein the amide is selected from the group consisting of urea, thiourea, formamide, biuret, triuret, thioformamide, dimethylformamide, ethyl formamide, and methyl formamide.

2. A composition formed by mixing (a) a reaction product of sulfuric acid and urea and (b) a compound selected from the group consisting of (2-chloroethyl)phosphonic acid and salts of (2-chloroethyl)phosphonic acid.

3. The composition of claim 2 wherein the reaction product is monocarbamide dihydrogen sulfate.

4. The composition of claim 2 wherein the molar ratio of urea to sulfuric acid is about ¼ to about ⅞.

5. A method for increasing the efficiency of a compound in controlling vegetation, the method comprising the step of applying to the vegetation a composition formed by mixing (a) a reaction product of sulfuric acid and an amide and (b) a compound, where the composition is applied at a rate such that a non-efficacious desiccating amount of the amide-sulfuric acid reaction product is applied per acre, the compound is selected from the group consisting of (2-chloroethyl)phosphonic acid and salts of (2-chloroethyl)phosphonic acid, and the amide is urea.

6. The method of claim 5 where the defoliation efficiency of the compound is increased.

7. The method of claim 5 where the plant growth regulator efficiency of the compound is increased.

8. The method of claim 5 where the growth inhibition efficiency of the compound is increased.

9. The method of claim 5 where the vegetation is cotton and the boll opening efficiency of the compound is increased.

10. The method of claim 5 where the vegetation is cotton and the defoliation efficiency of the compound is increased.

11. The method of claim 5 where the plant height stunting efficiency of the compound is increased.

12. The method of claim 5 where 18.75 pounds or less of the amide-sulfuric acid reaction product are applied per acre.

13. The method of claim 5 where about 15 pounds or less of the amide-sulfuric acid reaction product are applied per acre.

14. The method of claim 5 where about 12.5 pounds or less of the amide-sulfuric acid reaction product are applied per acre.

15. The method of claim 5 where about 10 pounds or less of the amide-sulfuric acid reaction product are applied per acre.

16. The method of claim 5 where about 7.8 pounds or less of the amide-sulfuric acid reaction product are applied per acre.

17. The method of claim 5 where about 5.2 pounds or less of the amide-sulfuric acid reaction product are applied per acre.

18. The method of claim 5 where 18.75 pounds or less of the amide-sulfuric acid reaction product are applied per acre, and the vegetation is selected from the group consisting of apples, barley, blackberries, bromeliads, cantaloupes, cherries, coffee, cotton, cranberries, cucumbers, figs, filberts, grapes, guava, lemons, Macadamia nuts, ornamentals, peppers, pineapples, rye, squash, tangerines, tangerine hybrids, tobacco, tomatoes, walnuts, wheat, rape, corn, flax, maize, oranges, peaches, rubber, and sugarcane.

19. The method of claim 5 where 18.75 pounds or less of the amide-sulfuric acid reaction product are applied per acre, and the vegetation comprises cotton.

20. The method of claim 5 where 18.75 pounds or less of the amide-sulfuric acid reaction product are applied per acre, the vegetation is cotton, and the action efficiency of the compound that is increased is defoliation.

21. A method for increasing the efficiency of a compound in controlling vegetation, the method comprising the step of applying to the vegetation a composition formed by mixing (a) a reaction product of sulfuric acid and an amide and (b) the compound, where the composition is applied at a rate such that a non-efficacious desiccating amount of the amide-sulfuric acid reaction product is applied per acre, the compound is selected from the group consisting of (2-chloroethyl)phosphonic acid and salts of (2-chloroethyl)phosphonic acid, and the amide is selected from the group consisting of urea, thiourea, formamide, biuret, triuret, thioformamide, dimethylformamide, ethyl formamide, and methyl formamide.

22. The method of claim 21 where 18.75 pounds or less of the amide-sulfuric acid reaction product are applied per acre.

23. The method of claim 21 where 18.75 pounds or less of the amide-sulfuric acid reaction product are applied per acre, and the vegetation is selected from the group consisting of apples, barley, blackberries, bromeliads, cantaloupes, cherries, coffee, cotton, cranberries, cucumbers, figs, filberts, grapes, guava, lemons, Macadamia nuts, ornamentals, peppers, pineapples, rye, squash, tangerines, tangerine hybrids, tobacco, tomatoes, walnuts, wheat, rape, corn, flax, maize, oranges, peaches, rubber, and sugarcane.

24. The method of claim 21 where 18.75 pounds or less of the amide-sulfuric acid reaction product are applied per acre, and the vegetation comprises cotton.

25. The composition of claim 1 where the amide is selected from the group consisting of urea, thiourea, formamide, biuret, triuret, dimethylformamide, and methyl formamide.

26. The method of claim 21 where the amide is selected from the group consisting of urea, thiourea, formamide, biuret, triuret, dimethylformamide, and methyl formamide.

* * * * *